US008258341B2

(12) United States Patent
Shtarov et al.

(10) Patent No.: US 8,258,341 B2
(45) Date of Patent: Sep. 4, 2012

(54) POLYFLUOROSULFONAMIDO AMINE AND INTERMEDIATE

(75) Inventors: Alexander Borisovich Shtarov, Wilmington, DE (US); Peter Michael Murphy, Chadds Ford, PA (US); Brent Ryan Gonska, Wilmington, DE (US); Stephan James McLain, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 511 days.

(21) Appl. No.: 12/500,817

(22) Filed: Jul. 10, 2009

(65) Prior Publication Data

US 2011/0009668 A1 Jan. 13, 2011

(51) Int. Cl.
*C07C 311/09* (2006.01)
(52) U.S. Cl. .............................. 564/96; 564/97
(58) Field of Classification Search .............. 564/96, 564/97
See application file for complete search history.

(56) References Cited

U.S. PATENT DOCUMENTS

| | | | |
|---|---|---|---|
| 3,708,538 A | 1/1973 | Hahn et al. | |
| 3,721,706 A | 3/1973 | Hoffmann et al. | |
| 4,069,158 A | 1/1978 | Bertocchio et al. | |
| 4,160,777 A | 7/1979 | Loudas | |
| 4,163,754 A | 8/1979 | Lew | |
| 4,166,065 A | 8/1979 | Beck | |
| 4,296,034 A | 10/1981 | Bouvet et al. | |
| 4,309,690 A | 1/1982 | Shoji et al. | |
| 4,424,133 A | 1/1984 | Mulligan | |
| 4,431,595 A | 2/1984 | Hashimoto et al. | |
| 4,486,391 A * | 12/1984 | Hashimoto | ............... 423/9 |
| 4,826,634 A | 5/1989 | Baasner et al. | |
| 4,836,281 A | 6/1989 | Robin et al. | |
| 4,983,769 A | 1/1991 | Bertocchio et al. | |
| 5,399,756 A | 3/1995 | Schneider et al. | |
| 5,514,493 A | 5/1996 | Waddell et al. | |
| 5,580,847 A | 12/1996 | Morikawa et al. | |
| 6,201,122 B1 | 3/2001 | Dams | |
| 6,518,345 B2 | 2/2003 | Tanaka et al. | |
| 6,960,410 B2 | 11/2005 | Kim et al. | |
| 2001/0001478 A1 | 5/2001 | Dams et al. | |
| 2001/0038949 A1 | 11/2001 | Hatazaki et al. | |
| 2003/0201419 A1 | 10/2003 | Tanaka et al. | |
| 2006/0177717 A1 | 8/2006 | Teasley et al. | |
| 2007/0093678 A1 | 4/2007 | Umemoto et al. | |
| 2008/0058538 A1 | 3/2008 | Matsunaga et al. | |
| 2009/0137831 A1 | 5/2009 | Rostovtsev | |
| 2009/0143598 A1 | 6/2009 | Herzog et al. | |

FOREIGN PATENT DOCUMENTS

| | | |
|---|---|---|
| CN | 1528479 A | 9/2004 |
| DE | 2004962 A1 | 9/1970 |
| EP | 0004919 A1 | 10/1979 |
| EP | 0211578 A2 | 2/1987 |
| EP | 0109023 B1 | 3/1987 |
| EP | 0636606 A1 | 2/1995 |
| EP | 1013311 A1 | 6/2000 |
| EP | 1083814 A1 | 4/2001 |
| FR | 2396586 A1 | 2/1979 |
| GB | 1304135 A | 1/1973 |
| JP | 5850971 A | 3/1983 |
| JP | 58038571 A | 3/1983 |
| JP | 58038569 B | 8/1983 |
| JP | 59230566 A | 12/1984 |
| JP | 60099272 A | 5/1985 |
| JP | 5235705 A | 9/1993 |
| JP | 5275406 A | 10/1993 |
| JP | 5275407 A | 10/1993 |
| NL | 197807188 A | 7/1978 |
| RO | 112612 B1 | 11/1997 |
| WO | 9003956 A1 | 4/1990 |
| WO | 9746283 A1 | 12/1997 |
| WO | 9929373 A1 | 6/1999 |
| WO | 0183037 A1 | 11/2001 |
| WO | 2008089391 A1 | 7/2008 |
| WO | 2010068531 A1 | 6/2010 |

OTHER PUBLICATIONS

A. Domanska et al., "Investigations Into the Synthesis of Fatty Acid Mono Amides of 1,2-Propanediamine", Tenside Detergents, 1980, 300-303, 17(6).
M. Kita, et al., "Reactions of Amines and Their Utilization II. Reactions of Methyl Esters of Fatty Acids With Ethylenediamine", Nippon Kagaku Kaishi, 1973, 2366-2370, (12). Translation of the Abstract of this Article is Located on p. 5 of this Current Article.
Lee et al., "Selective Mono-Boc Protection of Diamines", Synthetic Communications, 2007, 737-742, 37(5).
M. Naudet, et al., "Monoamides of Ethylenediamine.I. Reaction of Ethylenediamine With Fatty Acids and their Monoesters", Bulletin de la Societe Chimique de France, 1954, 1167-1172.
I.B. Romanova, et al., "Acylation of Aliphatic Diamines by Esters", Uzbekskii Khimicheskii Zhurnal 1971 43-46, 15 (4).
Y.V. Tanchuku, et al., "Reaction of Maleic Acid Esters With Ethylenediamine", Ukrainskii Khimicheskii Zhurnal (Russian Edition) 1976, 390-394, 42(4).

(Continued)

Primary Examiner — Peter G O Sullivan

(57) ABSTRACT

Current methods for making polyfluorosulfonamido amines, which involve the use of a diamine reactant, provide low yields and produce an undesirable fluorine containing bis-sulfonamide by-product representing an economic loss. The bis-sulfonamide by-product is particularly undesirable because it shares very similar physical properties with the desired monoamine product thus making isolation of the desired polyfluorosulfonamido amine product difficult and costly. Furthermore, instead of the efficient incorporation of fluorine to make the desired polyfluorosulfonamido amine product, the bis-sulfonamide by-product constitutes a substantial loss of costly fluorinated starting material. The bis-sulfonamide by-product also constitutes an undesirable impurity that can worsen surfactancy, repellency, or other performance characteristics of the desired polyfluorosulfonamido amine product. The present invention provides a method of making a polyfluorosulfonamido amine without the production of a bis-sulfonamide by-product by reacting a polyfluoroalkylsulfonic compound with a monoamino amide rather than with a diamine reactant as in previously known methods.

10 Claims, No Drawings

OTHER PUBLICATIONS

L.H. Amundsen, et al., "N-(Aminoalkyl)-Sulfanilamides and N-(Acetamidoalkyl)-Sulfanilamides", J. Am. Chem. Soc., 1946, 68 (4), 584-585, May 1, 2002.

S.R. Aspinall "A Synthesis of Tetrahydropyrimidines", J.Am. Chem. Soc., 1940, 62 (8), 2160-2162, May 1, 2002.

N.L. Drake, et al., "Synthetic Antimalarials. The Preparation of Certain 4-Aminoquinolines", J.Am. Chem. Soc., 1946, 68(7), 1208-1213, May 1, 2002.

M.H. Klingele, et al., "Synthesis and Some First-Row Transition-Metal Complexes of The 1,2,4-Triazole-Based BIS (Terdentate) Ligands TsPMAT and PMAT", Chem, Eur. J. 2005, 11, 6962-6973.

* cited by examiner

POLYFLUOROSULFONAMIDO AMINE AND INTERMEDIATE

FIELD OF THE INVENTION

The present invention relates to a method of making a polyfluorosulfonamido amine and the intermediate thereof.

BACKGROUND OF THE INVENTION

Polyfluorosulfonamido amines are useful starting materials for various products including: fluorinated surfactants, including cationic, non-ionic, anionic, and amphoteric surfactants; and fluorinated repellents, including (poly-(meth)acrylamides, ureas, imides. Specific applications for polyfluorosulfonamido amines include: electronics applications, nanotechnology, pharmaceutical and pesticide intermediates, catalysts, and firefighting foaming agents.

Rudimentary polyfluorosulfonamido amines can be generally described by the following formula:

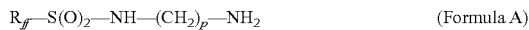
(Formula A)

wherein $R_f$ is chosen from a $C_4$ to $C_{12}$ polyfluoroalkyl; and p is an integer from 2 to 8.

Current methods for making polyfluorosulfonamido amines like those of Formula A provide low yields and produce an undesirable fluorine containing by-product representing an economic loss. For example U.S. Pat. No. 4,486,391 contemplates making polyfluorosulfonamido amines of Formula A by reacting a polyfluoroalkylsulfonic acid or an ester thereof with a diamine as represented by the following:

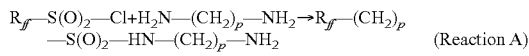
(Reaction A)

wherein $R_f$, and p are defined as above. Unfortunately, in addition to the desired monoamine product, Reaction A also produces an undesirable bis-sulfonamide by-product:

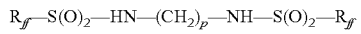

The bis-sulfonamide by-product is particularly undesirable because it shares very similar physical properties with the desired monoamine product thus making isolation of the desired monoamine product difficult and costly. Furthermore, instead of the efficient incorporation of fluorine to make the desired monoamine product, the bis-sulfonamide by-product constitutes a substantial loss of costly fluorinated starting material. The bis-sulfonamide by-product also constitutes an undesirable impurity that can worsen surfactancy, repellency, or other performance characteristics of the desired monoamine product.

Because of the aforementioned disadvantages, it would therefore be desirable to discover a method for making a polyfluorosulfonamido amine wherein the production of a bis-sulfonamide by-product is avoided.

BRIEF SUMMARY OF THE INVENTION

The present invention provides a method of making a polyfluorosulfonamido amine without the production of a bis-sulfonamide by-product thereby advantageously avoiding the need for its removal for the purpose of isolating the desired polyfluorosulfonamido amine. Furthermore, the present invention advantageously avoids or drastically reduces the production any by-product which contains fluorine. The present invention achieves the aforementioned advantages by reacting a polyfluoroalkylsulfonic compound with a monoamino amide rather than with a diamine as in previously known methods.

Polyfluorosulfonamido amines made by the present invention are represented by the following:

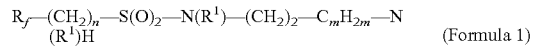
(Formula 1)

wherein:

$R_f$ is chosen from a $C_2$-$C_{12}$ polyfluoroalkyl optionally interrupted by one to four groups chosen from: —O—, —S—, and —S(O)$_2$—;

each $R^1$ is independently chosen from hydrogen or a $C_1$ to $C_6$ alkyl, preferably hydrogen;

n is chosen from an integer from 0 to 6, preferably less than 3, more preferably 2;

m is chosen from an integer from 0 to 10, preferably 0 to 2, more preferably 1.

The present invention makes the polyfluorosulfonamido amines of Formula 1 by a method comprising the reaction of polyfluoroalkylsulfonic compound with a monoamino amide followed by deacylation, preferably acid catalyzed deacylation.

The polyfluoroalkylsulfonic compounds useful in this invention are represented by the following:

(Formula 2)

wherein

X is chosen from hydroxyl, aryloxy, substituted aryloxy, or a halide, and more preferably chlorine; and n is defined as above.

The monoamino amides useful in this invention are represented by the following:

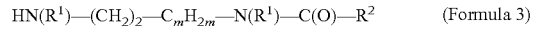
(Formula 3)

wherein each $R^1$ is independently chosen from hydrogen or a $C_1$ to $C_6$ alkyl, preferably hydrogen;

m is defined as above; and $R^2$ is chosen from hydrogen, a $C_1$ to $C_6$ alkyl, aryl, alkylaryl, or substituted aryl.

The monoamino amides useful in the invention can be made by reacting an ester with a diamine wherein:

i) the ester is represented by:

(Formula 4)

wherein $R^2$ is chosen from hydrogen, a $C_1$ to $C_6$ alkyl, aryl, alkylaryl, or substituted aryl;

wherein $R^3$ is chosen from a $C_1$ to $C_6$ alkyl, aryl, alkylaryl, or substituted aryl;

and ii) the diamine is represented by:

(Formula 5)

wherein each $R^1$ is independently chosen from hydrogen or a $C_1$ to $C_6$ alkyl, preferably hydrogen; and m is defined as above.

In accordance with the invention, a polyfluoroalkylsulfonic compound (Formula 2) is reacted with a monoamino amide (Formula 3) to make a polyfluorosulfonamide amide intermediate product represented by:

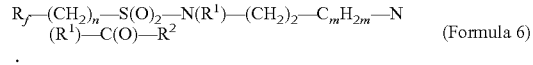
(Formula 6)

wherein $R_f$, n, $R^1$, m, and $R^2$ are defined as above.

The polyfluorosulfonamide amide intermediate product of Formula 6 is then subjected to deacylation to form the desired polyfluorosulfonamido amine of Formula 1.

Unless otherwise stated, the $R_f$ moiety referred to in Formula 1, Formula 2, and Formula 6 is chosen from a $C_2$-$C_{12}$ polyfluoroalkyl optionally interrupted by one to four groups chosen from: —O—, —S—, and —S(O)$_2$—. Examples of $R_f$ moieties include those chosen from a perfluoroalkyl without substitutions or interruptions include $(CF_3)_2CF$, and $CF_3(CF_2)_m$ wherein m is an integer from 1 to 11. Examples of $R_f$ moieties also include a perfluoroalkyl substituted by one hydrogen such as $(CF_3)_2CH$, $CF_3(CF_2)_2OCFHCF_2$, and $HC_mF_{2m}$ wherein m is 2 to 12. Examples of $R_f$ moieties also include a perfluoroalkyl which is interrupted by at least one oxygen such as $CF_3(CF_2)_2OCF_2CF_2$, $CF_3(CF_2)_2OCFHCF_2$, and $CF_3CF_2CF_2[OCF(CF_3)CF_2]_mOCRF$ wherein m is an integer from 6 to 15 and R can be F, $CF_3$, or H. Examples of $R_f$ moieties also include a $C_2$-$C_{12}$ perfluoroalkyl which is interrupted by at least one methylene such as $CF_3(CF_2)_3(CH_2CF_2)_m$ and $CF_3(CF_2)_5(CH_2CF_2)_m$ wherein m is 1, 2, or 3. Examples of $R_f$ moieties also include a perfluoroalkyl which is interrupted by at least one ethylene such as $F[(CF_2CF_2)_n(CH_2CH_2)_m]_kCF_2CF_2$ wherein n=1, 2, or 3 preferably 1; and m=1, or 2 preferably 1; and k=1, 2, or 3. Examples of $R_f$ moieties also include a polyfluoroalkyl which is interrupted by at least one sulfur (—S—) or sulfoxide (—SO2—) such as $CF_3(CF_2)_5CH_2CH_2SCH_2CH_2$, C6F13CH2CH2SO2CH2CH2, C6F13SCH2CH2.

DETAILED DESCRIPTION OF THE INVENTION

According to the method of the invention, the desired polyfluorosulfonamido amine product (Formula 1) is obtained by reacting a polyfluoroalkylsulfonic compound (Formula 2) with a monoamino amide (Formula 3) to form a polyfluorosulfonamide amide intermediate (Formula 6) which is subjected to deacylation. The various reactions resulting in the formation of the desired polyfluorosulfonamido amine product (Formula 1) may be represented as follows:

Reaction 1: formation of the monoamino amide of Formula 3

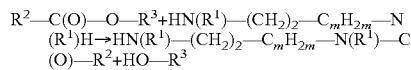

Reaction 2: formation of the polyfluorosulfonamide amide intermediate of Formula 6

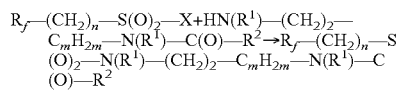

Reaction 3: formation of the polyfluorosulfonamido amine product of Formula 1 by deacylation

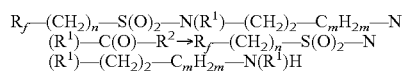

Referring to Reaction 1, the esters (Formula 4) useful in the formation of the monoamino amide of Formula 3 may be obtained commercially and methods for making such are well known in the art. Example of suitable esters for use in the invention include: methyl acetate, ethyl acetate, n-propyl acetate, 2-propyl acetate, n-butyl acetate, n-pentyl acetate, n-hexyl acetate, phenyl acetate, benzyl acetate, methyl formate, ethyl formate, n-propyl formate, methyl benzoate, ethyl benzoate, n-propyl benzoate, methyl hexanoate, ethyl hexanoate, n-propyl hexanoate.

Alternative examples of suitable esters for use in the invention are di-, tri-, or poly-carboxylic esters such as oxalate, malonate, succinate, phthalate, terephthalate; with specific examples including

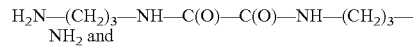

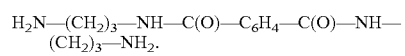

Referring to Reaction 1, the diamines (Formula 5) useful in the formation of the monoamino amide of Formula 3 may be obtained commercially and methods for making such are well known in the art. Example of suitable diamines for use in the invention include n-ethyl ethylene diamine; 1,3-diaminopropane; 1,4-diaminobutane; 1,5-diaminopentane; 1,6-diaminohexane; 1,8-diaminooctane; 1,5-diamino-2-methylpentane; n-ethyl ethylene diamine; n-propyl ethylene diamine; and N,N'-dimethyl-1,3-diaminopropane.

Referring to Reaction 1, the suitable reaction conditions for forming the monoamino amide of Formula 3 are exemplified by adding a diamine (Formula 5) to a reaction vessel (preferably under inert conditions, e.g., with nitrogen purge) equipped with mechanical stirrer and a condenser which returns any boiled material back to the vessel. The diamine is then heated while stirring. The temperature is chosen so that it is about 5 to 10° C. lower than the boiling point of the expected alcohol of Reaction 1. An ester (Formula 4) is then added slowly to the diamine over a period of about 15 to 90 minutes while maintaining the reflux temperature and stirring to create a reactant mixture. The total amount of ester added should yield a molar ratio of diamine:ester of preferably about 1:1, however this molar ratio can range between 5:1 to about 0.6:1. The reflux temperature is maintained until the reaction is complete as evidenced by the complete consumption of the ester, e.g., as measured by gas chromatography. A completed reaction typically occurs after about 2 to 24 hours. When the reaction is complete the reaction vessel typically contains a product mixture comprising lower boiling point components and higher boiling point components. The lower boiling point components include: possible residual unreacted ester, an alcohol by-product, possible water from contamination, any acid resulting from the reaction of the ester with water, and any unreacted diamine. The higher boiling point components include: the desired monoamino amide (Formula 3), and a bis-sulfonamide by-product resulting from the further reaction of the monoamino amide with the ester, said diamide by-product represented by:

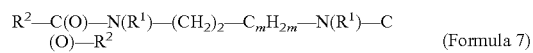
(Formula 7)

The lower boiling point components are removed from the product mixture by equipping the vessel with a distillation column and maintaining heat at a distillation temperature which causes the lower boiling point components to boil away while leaving behind the higher boiling point components. During distillation, the vessel can optionally be equipped with a vacuum source to reduce distillation pressure and temperatures. Typical distillation temperatures range from about 50 to 120° C. and can vary based upon the specific ester (Formula 4) and diamine (Formula 5) reactants chosen, the alcohol formed during the reaction, and the application of vacuum. It is important to remove unreacted diamine during the distillation of the lower boiling components to avoid the formation of an undesirable diamide by-product in Reaction 2, the diamide by-product represented by:

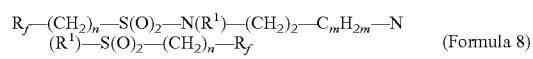
(Formula 8)

wherein $R_f$, n, $R^1$ are defined as above.

Referring to Reaction 2, the suitable reaction conditions for forming the polyfluorosulfonamide amide intermediate of Formula 6 are exemplified by dissolving a reactant comprising a monoamino amide (Formula 3) in a vessel (preferably under inert anhydrous conditions, e.g., with nitrogen purge) containing an appropriate aprotic solvent such methylene chloride, acetonitrile, dimethoxyethane, or tetrahydrofuran. The vessel is equipped with mechanical stirrer and a condenser. In addition to the monoamino amide, the reactant mixture can also comprise a diamide (Formula 7) which is a by-product of Reaction 1. The molar ratio of monoamino amide to diamide by-product should be preferably at least 1:1, more preferably at least 2:1, and most preferably at least 3:1. Preferably the reactant mixture comprises the higher boiling components of Reaction 1 as set forth above. The contents of the vessel are cooled to 0° C.; after which, a polyfluoroalkylsulfonic compound (Formula 2) is added to the vessel over a period of about 15 to 120 minutes while maintaining the temperature at 0° C. The molar ratio of monoamino amide (Formula 3) to the polyfluoroalkylsulfonic compound (Formula 2) is at least 2:1, the excess beyond the first molar equivalent of the monoamino amide is intended as a base to neutralize the acid generated in the reaction. If an additional base is used, then the molar ratio of monoamino amide (Formula 3) to the polyfluoroalkylsulfonic compound (Formula 2) can reduced to about 1:1. The contents of the vessel are then stirred for about 2 to 24 hours and allowed to warm to room temperature which results in a precipitation of typically colorless solids. The solids are filtered (removing the diamide by-product of Formula 7) and washed with water which dissolves and removes salt by-products created from the reaction of the monoamino amide with the acid. It is preferable that the water in the washing step comprises a surfactant which aids in wetting the solids. The isolated solid typically comprises from 50 to 90 weight % of the desired polyfluorosulfonamide amide intermediate (Formula 6).

Suitable reaction conditions for the formation of a polyfluorosulfonamido amine of Formula 1 as described in Reaction 3 above include conditions suitable for deacylation such as acid catalyzed deacylation. An example of acid catalyzed deacylation (also known as acid hydrolysis) dissolving a polyfluorosulfonamide amide intermediate (Formula 6) in a vessel (preferably under inert conditions, e.g., with nitrogen purge) containing an appropriate mixture of water and a polar solvent, preferably an alcohol, e.g., ethanol, or methanol, or an ether, e.g., 1,2-dimethoxyethane. The aforementioned solvents are preferable for the purpose of effectively reducing the foam formation as the hydrolysis proceeds, and allowing the deacylation reaction to proceed quickly to completion, with minimal by-products. The vessel is equipped with mechanical stirrer and a condenser which returns any boiled material back to the vessel. An acid (e.g., hydrochloric acid) is then added to the vessel between about 4:1 to 10:1 molar ratio of acid to polyfluorosulfonamido amine of Formula 1. The contents of the vessel are then heated to a temperature of from about 70 to about 100° C. The temperature is maintained until the reaction is complete as evidenced by the complete consumption of the polyfluorosulfonamide amide intermediate, e.g., as measured by gas chromatography. A completed reaction typically occurs after about 2 to 6 days. The amount of solvent is then reduced by about 80 weight % by distillation. The contents of the vessel are then cooled to about 25° C. and a strong base (e.g., NaOH, or KOH) is added until a pH of about 9 is achieved. Then an aqueous solution of precipitation agent (e.g., $MgSO_4$) is added to the vessel; typically comprising between 10 to 50 weight % of expected amount of polyfluorosulfonamido amine of Formula 1 causing the precipitation of a colorless solid The solid is then filtered and dried in a vacuum oven. The dried solid typically comprises from 60 to 95 weight % of the desired polyfluorosulfonamido amine of Formula 1.

EXAMPLES

The present invention is described in the foregoing example which is not intended to unduly restrict the invention as claimed.

Example 1

Preparation of 1,3-diaminopropane mono-acetamide 1,3-Diaminopropane mono-acetamide is an example of a monoamino amide (Formula 3) and was made by reacting an ester (methyl acetate) with a diamine (1,3-diaminopropane) as represented by the following:

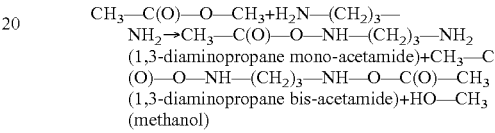

In a four-neck flask equipped with nitrogen purge, condenser, addition funnel and mechanical stirrer, about 125 grams (1.7 moles) of 1,3-diaminopropane (DAP) was added and heated to a temperature of 50° C. while stirring. Then about 82.9 grams (1.1 moles) of methyl acetate was added over 90 minutes while stirring. This reactant mixture was maintained at the reflux temperature of about 50° C. for about 18 hours after which all of the methyl acetate was consumed as determined by gas chromatography (GC) analysis. About 100 mL of dimethyl acetamide (DMAC) was added as a "chaser" to aid in the determination of proper distillation conditions. Then vacuum distillation was performed to remove all of the methanol and DAP as confirmed by GC analysis. GC analysis of the final product showed 19.5 weight % DMAC, 64.5 weight % 1,3-diaminopropane mono-acetamide, 16.0 weight % 1,3-diaminopropane bis-acetamide, and <0.1 weight % 1,3-diaminopropane.

Example 2

Preparation of N-[N'-acetyl-3-aminopropyl]-perfluorohexyl ethyl sulfonamide

N-[N'-acetyl-3-aminopropyl]-perfluorohexyl ethyl sulfonamide is an example of a polyfluorosulfonamide amide intermediate product (Formula 6) and was made by reacting a polyfluoroalkylsulfonic compound (perfluorohexyl ethyl sulfonyl chloride) with monoamino amide (1,3-diaminopropane mono-acetamide) as represented by the following:

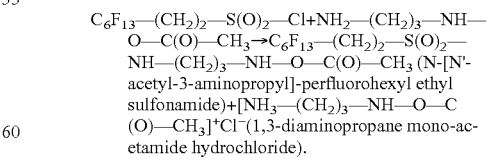

The final mixture obtained from the preparation of 1,3-diaminopropane mono-acetamide above (Example 1) was dissolved in 750 mL of acetonitrile in a four-neck flask equipped with nitrogen purge, condenser, addition funnel and mechanical stirrer. The dissolved mixture contained about 43.7 grams (0.38 moles) of 1,3-diaminopropane mono-acetamide, 1,3-diaminopropane bis-acetamide, and dimethyl acetamide. The mixture was cooled to about 0° C. Then about 120.1 grams (0.19 moles) of perfluorohexyl ethyl sulfonyl chloride as 70 weight % solution in toluene was added at 0° C. over 30 minutes while stirring. The mixture was stirred for an additional three hours and allowed to warn to room temperature producing a colorless solids which were filtered and washed with 1 liter of 0.1 weight % Zonyl® FSO-100 (a surfactant) in water to dissolve and remove 1,3-diaminopropane mono-acetamide hydrochloride. The remaining filtered colorless solid was analyzed by GC-mass spectrometry and proton NMR which confirmed the production of 89.5 grams (90% yield) of N-[N'-acetyl-3-aminopropyl]-perfluorohexyl ethyl sulfonamide.

Example 3

Preparation of
N-[3-aminopropyl]-2-(Perfluorohexyl)ethane
sulfonamide

N-[3-aminopropyl]-2-(Perfluorohexyl)ethane sulfonamide is an example of a polyfluorosulfonamido amines (Formula 1) and was made by the acid catalyzed deacylation (acid hydrolysis) of a polyfluorosulfonamide amide intermediate, N-[N'-acetyl-3-aminopropyl]-perfluorohexyl ethyl sulfonamide, as represented by the following:

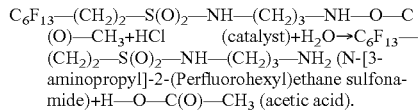

The final product obtained from the preparation of N-[N'-acetyl-3-aminopropyl]-perfluorohexyl ethyl sulfonamide above (Example 2) was dissolved in 170 grams of ethanol in a four-neck flask equipped with nitrogen purge, condenser, addition funnel and mechanical stirrer. The dissolved mixture contained about 56.9 grams (0.11 moles) of N-[N'-acetyl-3-aminopropyl]-perfluorohexyl ethyl sulfonamide. About 62 grams of 37 weight % hydrochloride acid in water was added while stirring. This mixture was heated to a reflux temperature of about 80° C. for about 5 days until all of the N-[N'-acetyl-3-aminopropyl]-perfluorohexyl ethyl sulfonamide was consumed as confirmed by GC. Then about 130 mL of ethanol/water/HCl was removed by distillation. The resulting mixture was allowed to cool to 25° C. and then the pH was adjusted to about 9 by addition of KOH. Then about 100 grams of 10 weight % aqueous $MgSO_4$ was added causing the precipitation of a colorless solid which was filtered and dried in a vacuum oven, which was analyzed by GC-mass spectrometry and proton NMR which confirmed the production of 45.1 grams (87% yield) of N-[3-aminopropyl]-2-(Perfluorohexyl)ethane sulfonamide.

What is claimed is:

1. A polyfluorosulfonamido amide intermediate product represented by:

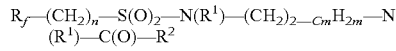

wherein:
$R_f$ is chosen from a $C_2$-$C_{12}$ polyfluoroalkyl optionally interrupted by one to four groups chosen from: —O—, —S—, and —S(O)$_2$—;
n is 2;
each $R^1$ is independently chosen from hydrogen or a $C_1$ to $C_6$ alkyl;
m is chosen from an integer from 0 to 10; and
$R^2$ is chosen from hydrogen, a $C_1$ to $C_6$ alkyl, aryl, alkylaryl, or substituted aryl.

2. The polyfluorosulfonamide amide intermediate product of claim 1 wherein $R_f$ is chosen from $C_6F_{13}$ or $C_4F_9$.

3. The polyfluorosulfonamide amide intermediate product of claim 1 wherein each $R^1$ is independently chosen from hydrogen or methyl or ethyl.

4. The polyfluorosulfonamide amide intermediate product of claim 1 wherein m is 1.

5. The polyfluorosulfonamide amide intermediate product of claim 1 wherein $R_f$ is chosen from $CF_3$—$(CF_2)_5$—, or $CF_3$—$(CF_2)_3$—, n is 2, each $R^1$ is hydrogen, m is 1, and $R^2$ is methyl or ethyl.

6. A method for making the polyfluorosulfonamide amide intermediate of claim 1, the method comprising reacting an polyfluoroalkylsulfonic compound with a monoamino amide under suitable conditions to make the polyfluorosulfonamide amide wherein:
i) the polyfluoroalkylsulfonic compound is represented by

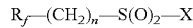

wherein X is chosen from hydroxyl, aryloxy, substituted aryloxy, or a halide; and
ii) the monoamino amide is represented by

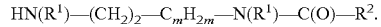

7. The method of claim 6 wherein X is chosen from a halide.

8. The method of claim 6 wherein the monoamino amide is made by reacting as ester with a diamine under suitable conditions to make to monoamino amide wherein:
i) the ester is represented by:

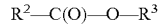

wherein
$R^3$ is chosen from a $C_1$ to $C_6$ alkyl, aryl, alkylaryl, or substituted aryl; and
ii) the diamine is represented by:

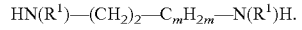

9. A method for making a polyfluorosulfonamido amine comprising subjecting the polyfluorosulfonamide amide intermediate of claim 1 to deacylation under suitable conditions to make the polyfluorosulfonamido amine wherein the polyfluorosulfonamido amine is represented by

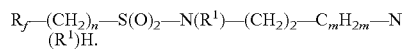

10. The method of claim 9 wherein the deacylation is acid catalyzed deacylation which comprises the reduction of foam generation by dissolving the polyfluorosulfonamide amide intermediate in an aqueous solvent comprising alcohol or ether, or both.

* * * * *